US010219486B2

(12) United States Patent
Eggink et al.

(10) Patent No.: US 10,219,486 B2
(45) Date of Patent: Mar. 5, 2019

(54) PEPPER WITH ALTERED FLAVOR ATTRIBUTES AND ODOR INTENSITY

(71) Applicant: RIJK ZWAAN ZAADTEELT EN ZAADHANDEL B.V., De Lier (NL)

(72) Inventors: Pieter Martijn Eggink, De Lier (NL); Jacob Pieter Willem Haanstra, De Lier (NL); Evert Willem Gutteling, De Lier (NL); Arnaud Guillaume Bovy, De Lier (NL); Yury Tikunov, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 6 days.

(21) Appl. No.: 14/980,084

(22) Filed: Dec. 28, 2015

(65) Prior Publication Data

US 2016/0160225 A1   Jun. 9, 2016

Related U.S. Application Data

(63) Continuation-in-part of application No. PCT/EP2014/064119, filed on Jul. 2, 2014.

(30) Foreign Application Priority Data

Jul. 2, 2013 (EP) ..................... 13174795

(51) Int. Cl.
| | | |
|---|---|---|
| *A01H 5/08* | (2018.01) | |
| *A01H 1/04* | (2006.01) | |
| *C12Q 1/68* | (2018.01) | |
| *A01H 6/82* | (2018.01) | |
| *C12Q 1/6827* | (2018.01) | |
| *C12Q 1/6895* | (2018.01) | |
| *A01H 5/00* | (2018.01) | |
| *A23L 19/00* | (2016.01) | |

(52) U.S. Cl.
CPC .............. *A01H 6/822* (2018.05); *A01H 1/04* (2013.01); *C12Q 1/6827* (2013.01); *C12Q 1/6895* (2013.01); *A01H 5/00* (2013.01); *A01H 5/08* (2013.01); *A23L 19/00* (2016.08); *C12Q 2600/13* (2013.01); *C12Q 2600/156* (2013.01)

(58) Field of Classification Search
None
See application file for complete search history.

(56) References Cited

PUBLICATIONS

Lefebvre et al. Genome 38: 112-121 (1995).*
Kollmannsberger et al. Journal of the Science of Food and Agriculture 91: 1598-1611 (2011).*
Paran et al. Molecular Biology 13: 251-261 (2004).*
Eggink et al. Food Chemistry 132(1): 301-310 published online Oct. 2011; Supplemental Tables 1&2 Only.*
Eggink et al. Theoretical and Applied Genetics 127(2): 373-390 (2014).*
Chae et al. Capsicum and Eggplant Newsletter 22: 121-124 (2003).*
Albrecht et al. HortScience 45(8): S289-S290 (Aug. 2010).*
Moreno et al. Scientia Horitculturae 135: 87-89 (Feb. 2012).*
Lefebvre et al. Theoretical and Applied Genetics 107: 661-666 (2003).*
Ben Chaim et al. Theoretical and Applied Genetics 102: 1016-1028 (2001).*
Wu et al. Theoretical and Applied Genetics 118: 1279-1293 (2009).*
Kim et al. Weon'ye Gwahag Gi'sulji 28(6): 1014-1024 (2010), Abstract Only.*
International Search Report and Written Opinion of the International Searching Authority dated Oct. 17, 2014, which issued during prosecution of International Application No. PCT/EP2014/064119.
Database EMBL "KS17046C11 KS17 Capsicum annuum cDNA, mRNA sequence" Retrieved from EBI Accession No. EM_EST:GD079793, Mar. 8, 2009.
Eggink, et al. "A taste of sweet pepper: Volatile and non-volatile chemical composition of fresh sweet pepper (*Capsicum annuum*) in relation to sensory evaluation of taste" Food Chemistry 132(1):301-310, Oct. 2011.
Lu, et al. SNP Marker Integration and QTL Analysis of 12 Agronomic and Morphological Traits in F8 RILs of Pepper (*Capsicum annuum* L.) Molecules and Cells 34(1):25-34, Jul. 2012.
Minamiyama, et al. "AN SSR-based linkage map of Capsicum annuum" Molecular Breeding 18(2):157-169, Aug. 2006.
Yoon, et al. "Overcoming Two Post-fertilization Genetic Barriers in Interspecific Hybridization between Capsicum annuum and C. baccatum for Introgression of Anthracnose Resistance" Breeding Science 56(1):31-38, Mar. 2006.
Chinese Third Office Action dated Jan. 4, 2018 which issued during prosecution of Chinese Application No. 201480037559.
Lihao "Genetic and QTLs Analysis of the Fertility Restorer of Cytoplamic Male Sterility in Pepper (*Capsicum annuum* L.) and Breeding of Fertility Restorer Lines" Chinese Academy of Agricultural Sciences Ph.D. Dissertation Jun. 2007.

* cited by examiner

*Primary Examiner* — David T Fox
(74) *Attorney, Agent, or Firm* — Duane Morris LLP; Thomas J. Kowalski; Deborah L. Lu

(57) ABSTRACT

The present invention relates to a pepper plant (*Capsicum annuum* L.) which may comprise a QTL that leads to the plant producing fruits that have a novel flavor, which QTL is obtainable from a pepper plant which may comprise said QTL, representative seed of which was deposited with the NCIMB under accession number NCIMB 42137.

33 Claims, 2 Drawing Sheets
Specification includes a Sequence Listing.

Figure 1.

| LG | cM | Marker | NIL37 | NIL46 | NIL39 | NIL38 | NIL48 | NIL40 | GNM | QTL |
|---|---|---|---|---|---|---|---|---|---|---|
| 3 | 0 | CA-0620 | A | A | A | A | A | A | A | |
| | 19.6 | CA-0428 | A | A | A | A | A | A | A | |
| | 32.93 | SEQ ID NO:1 | B | H | B | B | H | H | A | Flavor |
| | 33.27 | SEQ ID NO:3 | B | H | B | B | H | H | A | |
| | 32.28 | SEQ ID NO:5 | B | H | B | B | H | H | A | |
| | 33.32 | SEQ ID NO:7 | B | H | B | B | H | H | A | |
| | 33.40 | SEQ ID NO:9 | B | H | B | B | H | H | A | |
| | 33.41 | SEQ ID NO:11 | B | H | B | B | H | H | A | |

PEPPER WITH ALTERED FLAVOR ATTRIBUTES AND ODOR INTENSITY

RELATED APPLICATIONS AND INCORPORATION BY REFERENCE

This application is a continuation-in-part application of international patent application Serial No. PCT/EP2014/064119 filed 2 Jul. 2014, which published as PCT Publication No. WO 2015/000993 on 8 Jan. 2015, which claims benefit of European patent application Serial No. 13174795.8 filed 2 Jul. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Nov. 23, 2015, is named 43104002231SL.txt and is 4,296 bytes in size.

FIELD OF THE INVENTION

The invention relates to pepper plants producing fruits with a novel flavor. Furthermore the invention relates to the use of plants, seeds and propagation material from the pepper plant as germplasm in a breeding program aimed at acquiring pepper plants producing fruits with the novel flavor.

BACKGROUND OF THE INVENTION

Sweet and hot pepper plants belong to the genus *Capsicum* which is part of the Nightshade family (Solanaceae). *Capsicum* species are native to South America, Middle America and a part of North America, where they have been cultivated for thousands of years, and are now cultivated worldwide. Several of the members of the *Capsicum* genus are used as spices, vegetables, and/or medicines.

The species *Capsicum annuum* L. is the most common and extensively cultivated of the five domesticated *Capsicum* species (*Capsicum annuum, Capsicum baccatum, Capsicum pubescens, Capsicum chinense, Capsicum frutescens*). It may comprise several cultivar groups among which bell pepper (also named paprika) is the most commonly grown in northern Europe and the USA. Bell pepper fruits are eaten raw, cooked, immature and mature and may be processed into powders, sauces, and salsas. The fruits are mostly green in the immature stage, but during ripening they become red, yellow, orange, purple or brown. Sweet pepper may comprise any pepper plant, such as bell pepper plants, having mild non-pungent fruits. Pepper plants can be cultivated in the open field, greenhouse, tunnel or shade house under a wide range of climatic conditions, but they perform best in warm and dry conditions.

Flavor is an important quality parameter for fruits and vegetables. External qualities such as color, texture and shape are relatively easy to evaluate by both producers and consumers. The evaluation of flavor attributes, however, is more complex. Flavor is the sensory impression of a substance. The flavor of food, as perceived during consumption may be defined as the overall sensation provided by the interaction of taste, odor (which may also be indicated as smell, fragrance or aroma), mouthfeel, sight and sound. Mouthfeel, sight and sound are physical or indirect senses, which influence taste and smell, and therefore influence food acceptance. The remaining sensations are responses of the chemical senses and can globally be divided into two groups, i.e. compounds responsible for taste and compounds responsible for odor. Compounds belonging to the first group are mainly non-volatile at room temperature and interact with taste receptors in the oral cavity and especially on the tongue. Compounds belonging to the other group are volatile and are perceived by the odor receptors in olfactory cells in the nasal cavity. The odor of food can be smelled both when it is outside and inside the mouth. When we have food in our mouth odor molecules can easily travel from the mouth to the odor receptors in the nasal cavity via the connection between the throat and the nasal cavity. This type of perception of flavors is called retronasal sense of smell.

Although the flavor of some fruit crops, like tomato, strawberry, peach or melon, has been researched extensively, only a limited amount of research has been performed on the flavor of fruits of *Capsicum* species. Research on pepper fruit flavor has mainly focused on the characterization of volatile and non-volatile component variation in cultivated and/or wild species. However, correlations between flavor components and sensory evaluations by taste or odor panels are generally missing.

Pepper fruits are commonly used in the diet because of their typical colors, pungency, taste and/or distinct aroma. Pepper fruits are eaten fresh or processed, as unripe (green or white) or ripe (e.g. red, yellow and orange) fruits. In the breeding of pepper, the factors production and quality (e.g. shelf life, firmness and disease resistances) are of main interest. However, since consumers have become more critical, attention in pepper, like in tomato, is shifting towards flavor as an important quality parameter.

Citation or identification of any document in this application is not an admission that such document is available as prior art to the present invention.

SUMMARY OF THE INVENTION

It is therefore the object of the present invention to provide novel pepper plants which produce fruits with a new and different flavor.

In the research leading to the invention a new pepper plant was developed that was found to produce fruits with a surprising new flavor. It was found that the surprisingly different flavor correlated with the presence in the *Capsicum annuum* genome of an introgression from *Capsicum baccatum*, identified herein as a Quantitative Trait Locus (QTL). The QTL that causes the novel flavor is as present in the genome of plants grown from seeds which were deposited at the NCIMB under accession number NCIMB 42137. The QTL is located on Linkage Group 3 (LG3) and in the genome of plants grown from seeds of deposit NCIMB 42137 is linked to at least one marker selected from the group consisting of SEQ ID No:1, SEQ ID No:3, SEQ ID No:5, SEQ ID No:7, SEQ ID No:9 and SEQ ID No:11 (Table 1). Preferably, the pepper plant of the invention is a sweet pepper.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of *Capsicum annuum* L. line 12R.6869-00 that may comprise the QTL of the invention which leads to the pepper plant producing fruits that have a surprising new flavor, were deposited with NCIMB Ltd, Ferguson Building, Craibstone Estate, Bucksburn, Aberdeen AB21 9YA, UK, on Apr. 12, 2013 under deposit accession number NCIMB 42137. Seeds of this deposit may comprise the QTL in a homozygous state.

The deposited seeds do not meet the DUS criteria which are required for obtaining plant variety protection, and can therefore not be considered to be plant varieties.

The Deposits with NCIMB Ltd, under deposit accession number NCIMB 42137 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Graphical representation of the QTL of the invention on LG3. Only regions with *C. baccatum* fragments are indicated. *C. baccatum* introgressions are indicated with their markers as B (homozygous, in bold) or H (heterozygous, i.e. segregating in the ML), while the *C. annuum* genomic background is indicated with A.

DETAILED DESCRIPTION OF THE INVENTION

Figure 2:
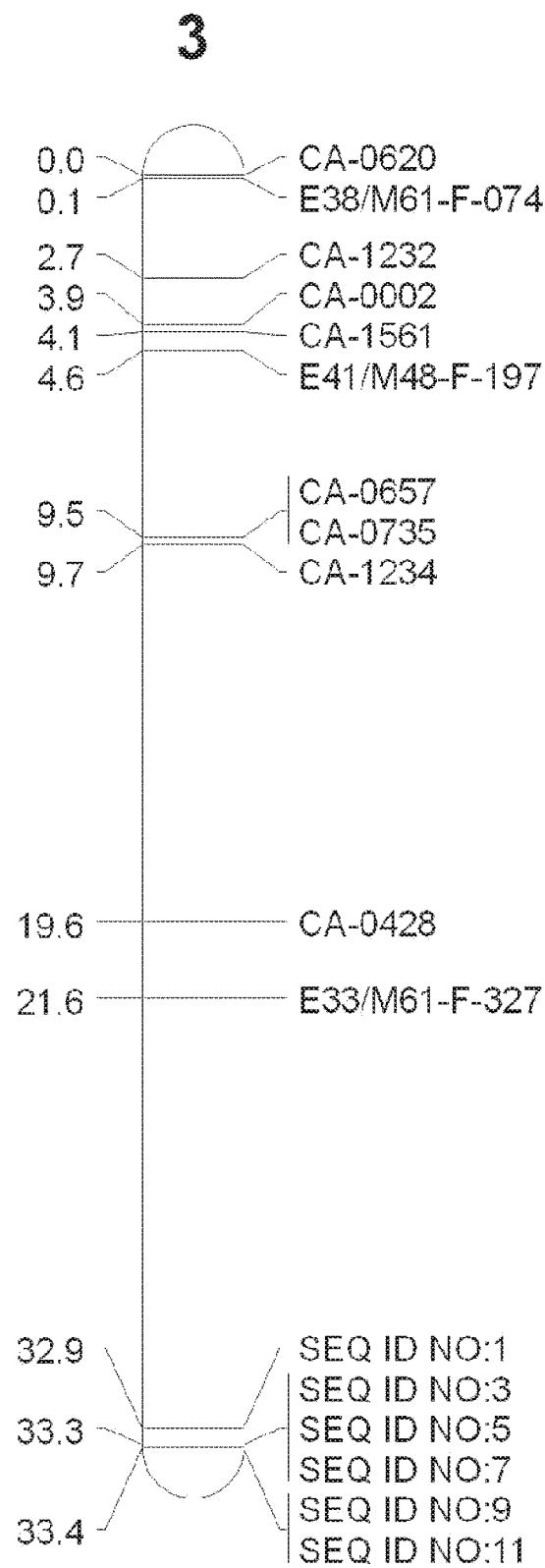
FIG. 2: Genetic map of the *C. annuum*×*C. baccatum* BC2 population Linkage Group3 (LG3).

The development of the initial plants with the novel flavor is described in Example 1. In short, *Capsicum baccatum* var. *pendulum* was used as a donor parent for backcrossing (BC) with two cultivated *C. annuum* blocky breeding lines (SM and GNM). Further to this initial cross $BC_2S_1$ lines and near-isogenic lines (NILs) were developed that were further tested for flavor and in some of these lines plants with a surprising new flavor were identified.

Pepper plants of the invention have a small introgression on LG3 from *Capsicum baccatum*, the QTL of the invention. Nomenclature of linkage groups is referred to the consensus chromosome numbers as in Wu et al. (Theor. Appl. Genet. (2009) 118, 1279-1293). The flavor effect of this small introgression on LG3 is evident and an enrichment of the flavor variation within *Capsicum annuum*. The size of the introgression fragment, 0.5 cM, is based on the genetic map (FIG. 2) developed within the research leading to this invention. Such relatively small introgression size, in combination with the availability of in-fragment markers and absence of linkage drag, facilitates its use in breeding.

It was found that in the genome of plants grown from seeds of the deposit each of the markers SEQ ID No:1, SEQ ID No:3, SEQ ID No:5, SEQ ID No:7, SEQ ID No:9 and SEQ ID No:11 (full sequence data given in Table 1) is linked to the QTL that causes the novel flavor of the invention (FIG. 1). Although any of these markers or any combination of these markers may be used for identifying the QTL causing the invented trait of novel flavor, marker SEQ ID NO:3 is preferred because it had the highest LOD score in the statistical tests. The QTL causing the invented trait of novel flavour may be identified using the combination of markers SEQ ID No:1, SEQ ID No:3, SEQ ID No:5, SEQ ID No:7, SEQ ID No:9 and SEQ ID No:11, the combination of markers SEQ ID No:1, SEQ ID No:3, SEQ ID No:5, SEQ ID No:7 and SEQ ID No:9, the combination of markers SEQ ID No:1, SEQ ID No:3, SEQ ID No:5 and SEQ ID No:7, the combination of markers SEQ ID No:1, SEQ ID No:3 and SEQ ID No:5, the combination of markers SEQ ID No:1 and SEQ ID No:3, the combination of markers SEQ ID No:3, SEQ ID No:5, SEQ ID No:7, SEQ ID No:9 and SEQ ID No:11, the combination of markers SEQ ID No:3, SEQ ID No:5, SEQ ID No:7 and SEQ ID No:9, the combination of markers SEQ ID No:3, SEQ ID No:5 and SEQ ID No:7, the combination of markers SEQ ID No:3 and SEQ ID No:5. In particular, the QTL causing the invented trait of novel flavour can be identified using the combination of markers SEQ ID No:3, SEQ ID No:5, SEQ ID No:7, SEQ ID No:9 and SEQ ID No:11, more in particular SEQ ID No:3, SEQ ID No:5 and SEQ ID No:7, and most in particular SEQ ID No:3 and SEQ ID No:5.

The QTL is thus present in the genome of the deposited material and this material is thus a source of the QTL that can be used to introduce the novel flavor trait into other pepper plants of the species *Capsicum annuum*. Such plants may be used as a starting point to develop further varieties with the novel flavor. Another possible source of the QTL of the invention, the introgression fragment on LG3, is *Capsicum baccatum*. *Capsicum baccatum*, in particular *Capsicum baccatum* var. *pendulum*, may be used as a source of the genomic fragment, the QTL of the invention, to introduce the novel flavor trait into pepper plants. This is facilitated by the availability of in-fragment markers. Any *Capsicum annuum* pepper plant which may comprise the QTL of the invention, regardless of the source of this QTL, is a plant of the invention. A *Capsicum annuum* pepper plant which may comprise the QTL of the invention, wherein this QTL was introduced into this pepper plant from a pepper plant of the invention, for example from a plant grown from seed of deposit NCIMB 42137, is therefore the same or equivalent to a *Capsicum annuum* pepper plant which may comprise the QTL of the invention, wherein this QTL was introduced into this pepper plant from a *Capsicum baccatum* plant, in particular a *Capsicum baccatum* var. *pendulum* plant.

In the deposited seeds, the genetic determinant is linked with each of the molecular markers SEQ ID No:1, SEQ ID No:3, SEQ ID No:5, SEQ ID No:7, SEQ ID No:9 and SEQ ID No:11. These markers may also be linked to the QTL that may have in either or both pepper plants that are used as parents in a cross to transfer the novel flavor trait to other plants, but the presence of at least one of the mentioned markers is not essential as long as the QTL causing the trait is present. The presence of the novel flavor phenotype is a direct indicator that the QTL of the invention is present since the QTL is the genetic information that encodes the novel flavor trait. Thus, a plant of the invention which has the novel flavor trait as described herein is still a plant of the invention when the QTL underlying the phenotype is present therein but the markers no longer are. Markers are sometimes but not always the genetic cause of a trait. Markers may be located in the gene that causes the trait or are genetically linked to it. They are often used as tools to follow the inheritance of the trait. During breeding, the molecular markers that in the deposited seeds are linked to the genetic determinant may be thus used to assist transfer of the novel flavor trait to other plants. A skilled breeder would understand that the transfer of the novel flavor trait into a pepper plant may be monitored by the use of sensory and/or biochemical analysis, or by monitoring and breeding for the presence of molecular markers as described herein (i.e. marker assisted selection), or both. Localization of such markers to specific genomic regions further allows for the use of associated sequences in breeding and for the development of additional linked genetic markers. It will be understood to those skilled in the art that other markers or probes linked to the chromosomal region of the introgression fragment on LG3 as identified herein could be employed to identify plants which may comprise the QTL of the invention. Knowledge of the chromosomal region of the present invention facilitates introgression of the novel flavor trait of the invention from plants which may comprise the QTL of the invention, such as plants grown from the deposited seeds or *Capsicum baccatum* plants, in particular *Capsicum baccatum* var. *pendulum* plants, into other pepper plants. Linkage blocks of various sizes could be transferred within the scope of this invention as long as the chromosomal region confers the novel flavor of the invention. Accordingly, it is emphasized that the present invention may be practiced using any molecular markers that genetically map within the identified region provided that the markers are polymorphic between the parents.

The present invention thus provides a pepper plant (*Capsicum annuum* L.) that produces fruits with a novel flavor, wherein the pepper plant may comprise a QTL which when present leads to the novel flavor and wherein the QTL is as present in the genome of, or obtainable from, *Capsicum baccatum* or pepper plants grown from seeds which were deposited at the NCIMB under accession number NCIMB 42137. The QTL is located on LG3 and said QTL is the same as a QTL that is found in the genome of plants grown from seeds of deposit NCIMB 42137 and is linked therein to at least one marker selected from the group consisting of SEQ ID No:1, SEQ ID No:3, SEQ ID No:5, SEQ ID No:7, SEQ ID No:9 and SEQ ID No:11.

As used herein pepper plants are *Capsicum annuum* plants. It is understood that a *Capsicum annuum* (pepper) plant is phenotypically identifiable as such, though said plant may contain introgressions from other *Capsicum* species in its genome. The skilled pepper breeder or grower knows how to distinguish *Capsicum annuum* plants and fruits from plants and fruits belonging to other *Capsicum* species.

The surprising new flavor was established by a professional and independent taste panel. The descriptive analysis of pepper fruits showing the new flavor took place in a sensory laboratory at Wageningen UR Greenhouse Horticulture in Bleiswijk, The Netherlands. Thirteen panelists, who were part of a trained panel with broad experience in sensory evaluations of food products, including pepper, took part in the experiment.

Two different sensory tests were done, one with 34 $BC_2S_1$ lines and one with 20 NILs, derived from three of these $BC_2S_1$ lines. Due to its severe pungency, the *C. baccatum* var. *pendulum* parent of the initial cross was not included in the sensory evaluations. No information was provided to the panel about the genotypes.

During training sessions using the fruits of publicly available pepper varieties, some weeks prior to the $BC_2S_1$ test, the panelists agreed on fourteen attributes to describe the flavor sensation in the mouth, which were the texture attributes crunchiness, stickiness of the skin, toughness and juiciness, the basic taste attributes sweetness and sourness and the retronasal flavor attributes aroma intensity, grassiness, green bean, carrot, fruity/apple, perfume, petrochemical and musty.

During the sensory evaluation of the fruits in the $BC_2S_1$ experiment it became clear that the vocabulary (i.e. the predefined attributes) of the trained panel was not sufficient to cover all the flavor variation. Therefore, in the training sessions some weeks prior to the sensory test for the NILs, the test panel was trained with both fruits from publicly available pepper varieties and fruits from preselected NILs having more divergent flavors. This resulted in the addition of the flavor attributes flowers, non-pungent spices, celery, chives and bitter, while the attribute perfume was no longer used in the NILs sensory test.

The fruits produced by plants having the said QTL of the invention on LG3, show a significantly higher score for the flavor attributes aroma, flowers, spices, celery and chives, and a lower score for the attribute grassiness. The said effects are strongest when determined in the fruits of plants that have the QTL on LG3 in a homozygous state. In the fruits of plants that have the QTL on LG3 in a heterozygous state, the scores for said flavor attributes are intermediate between those of pepper fruits of plants without the said QTL of the invention and fruits of plants wherein the QTL of the invention is present in a homozygous state.

For the BC₂S₁ lines the sensory attribute odor intensity (smelled through the nose, i.e. orthonasal) was evaluated and all BC₂S₁ lines were scored on an odor intensity scale ranging from 0 for no odor to 7 for an odor intensity similar to that found in fruits of the *C. baccatum* var. *pendulum* parent line, by three untrained persons.

Fruits of pepper plants of the invention score higher on an odor intensity scale on which higher values represent a more intense odor, as compared to fruits at a similar ripening stage from isogenic pepper plants not carrying the QTL of the invention.

The flavor of fruits of plants of the invention may also be described as a 'tropical flavor' and/or 'chives flavor' and/or 'similar to papaya'.

The flavor of the fruits of the *C. baccatum* parent line was tested separately by a group of untrained persons accustomed to eat pungent food. This group described the taste of fruits of the *C. baccatum* var. *pendulum* parent line as fruity, not very aromatic and sour. This is in clear contrast with the much larger variation in flavors found in plants of the invention, and makes the effect the introgression of *C. baccatum* has in plants of the invention very unexpected.

The novel flavor of pepper fruits of the invention is thus defined as the pepper fruits having higher scores for one or more flavor attributes selected from the group consisting of aroma, flowers, non-pungent spices, celery and chives, and/or having a lower score for the flavor attribute grassiness, and optionally a higher odor intensity, as compared to pepper fruits at a similar ripening stage from isogenic pepper plants not carrying said QTL.

Preferably, pepper fruits having the novel flavor of the invention have higher scores for the flavor attributes aroma, celery and chives, optionally have higher scores for one or more of the flavor attributes selected from the group consisting of flowers and non-pungent spices, optionally have a lower score for the flavor attribute grassiness, and optionally a higher odor intensity, as compared to pepper fruits at a similar ripening stage from isogenic pepper plants not carrying said QTL.

Preferably, pepper fruits having the novel flavor of the invention have higher scores for the flavor attributes selected from the group consisting of aroma, flowers, non-pungent spices, celery and chives, and have a lower score for the flavor attribute grassiness, and optionally a higher odor intensity, as compared to pepper fruits at a similar ripening stage from isogenic pepper plants not carrying said QTL.

It is clear that a trained taste panel analyzing the flavor of the pepper fruits of plants of the invention using said flavor attributes is able to recognize and identify the novel flavor of pepper fruits of the invention.

As the ripening stage affects the flavor and biochemical characteristics of pepper fruits, it is understood that comparisons between pepper plants carrying the QTL of the invention with pepper plants not carrying this QTL should be made between plants of a similar fruit ripening stage, for example at a fully mature and ripe stage in which the pepper fruits are 95-100% colored, as mentioned in example 2.

Besides looking at genetic aspects of the observed flavor variation, the responsible biochemical compounds were identified. This biochemical profiling revealed that five volatiles could be identified and mapped to the LG3 QTL region that caused the novel flavor. Three metabolites out of these five could be confirmed in the NILs. The peak representing either artemisia ketone or 6-methyl-4-oxo-5-heptenal showed a strong increase in intensity in presence of the QTL, while the compounds (Z)-butanoic acid 3-hexenyl ester and 2-isobutyl-3-methoxypyrazine were decreased in NILs having the QTL. The peak representing either artemisia ketone or 6-methyl-4-oxo-5-heptenal that was confirmed to be specifically up-regulated in the LG3 QTL containing NILs and BC2S1 plants, at the same time shows a strong correlation with odor. Said peak represents either artemisia ketone or 6-methyl-4-oxo-5-heptenal, and preferably represents the compound artemisia ketone.

Having a closer look at the six LG3 QTL containing NILs it turned out that the intensity of the two down-regulated compounds, (Z)-butanoic acid 3-hexenyl ester and 2-isobutyl-3-methoxypyrazine, was only decreased in the homozygous NILs and not in the heterozygous NILs (see Table 2). An effect of 2-isobutyl-3-methoxypyrazine alone on aroma was not found, as NILs with a significantly decreased or increased intensity were unaffected for aroma intensity.

A follow-up experiment in which sub-NILs having the LG3 QTL were compared to sub-NILs without the QTL, resulted in the confirmation of the LG3 QTL flavor effect. Samples with the LG3 flavor QTL were again lower in 2-isobutyl-3-methoxypyrazine, higher in the compound that is either artemisia ketone or 6-methyl-4-oxo-5-heptenal, and higher in some lipid derived volatiles: (E)-2-hexenal, (Z)-2-hexen-1-ol, 1-penten-3-ol, hexanal, (Z)-2-penten-1-ol and (E)-2-pentenal.

According to the invention fruits of the pepper plant of the invention have a higher amount of artemisia ketone and/or a higher amount of 6-methyl-4-oxo-5-heptenal and/or a higher amount of (E)-2-hexenal and/or a higher amount of (Z)-2-hexen-1-ol and/or a higher amount of 1-penten-3-ol and/or a higher amount of hexanal and/or a higher amount of (Z)-2-penten-1-ol and/or a higher amount of (E)-2-pentenal and/or a lower amount of (Z)-butanoic acid 3-hexenyl ester and/or a lower amount of 2-isobutyl-3-methoxypyrazine compared to fruits of a similar ripening stage from an isogenic pepper plant not comprising said QTL.

Preferably, fruits of the pepper plant of the invention have a higher amount of artemisia ketone or 6-methyl-4-oxo-5-heptanal, and optionally a lower amount of one or more compounds selected from the group consisting of (Z)-butanoic acid 3-hexenyl ester and 2-isobutyl-3-methoxypyrazine, and/or optionally a higher amount of one or more compounds selected from the group consisting of (E)-2-hexenal, (Z)-2-hexen-1-ol, 1-penten-3-ol, hexanal, (Z)-2-penten-1-ol and (E)-2-pentenal, compared to fruits of a similar ripening stage from an isogenic pepper plant not comprising said QTL.

Preferably, fruits of the pepper plant of the invention carrying the QTL of the invention homozygously have a higher amount of artemisia ketone or 6-methyl-4-oxo-5-heptanal and a lower amount of one or more compounds selected from the group consisting of (Z)-butanoic acid 3-hexenyl ester and 2-isobutyl-3-methoxypyrazine, and optionally a higher amount of one or more compounds selected from the group consisting of (E)-2-hexenal, (Z)-2-hexen-1-ol, 1-penten-3-ol, hexanal, (Z)-2-penten-1-ol and (E)-2-pentenal, compared to fruits of a similar ripening stage from an isogenic pepper plant not comprising said QTL.

Preferably, fruits of the pepper plant of the invention carrying the QTL of the invention homozygously have a higher amount of artemisia ketone or 6-methyl-4-oxo-5-heptanal and a lower amount of one or more compounds selected from the group consisting of (Z)-butanoic acid 3-hexenyl ester and 2-isobutyl-3-methoxypyrazine, and a higher amount of one or more compounds selected from the group consisting of (E)-2-hexenal, (Z)-2-hexen-1-ol, 1-penten-3-ol, hexanal, (Z)-2-penten-1-ol and (E)-2-pentenal, compared to fruits of a similar ripening stage from an isogenic pepper plant not comprising said QTL.

In a further embodiment, fruits of the pepper plant of the invention carrying the QTL of the invention homozygously have a higher amount of artemisia ketone or 6-methyl-4-oxo-5-heptanal and a lower amount of the compounds (Z)-butanoic acid 3-hexenyl ester and 2-isobutyl-3-methoxypyrazine, and a higher amount of the compounds (E)-2-hexenal, (Z)-2-hexen-1-ol, 1-penten-3-ol, hexanal, (Z)-2-penten-1-ol and (E)-2-pentenal, compared to fruits of a similar ripening stage from an isogenic pepper plant not comprising said QTL.

In a further embodiment, fruits of the pepper plant of the invention have a higher amount of artemisia ketone or 6-methyl-4-oxo-5-heptanal, and a higher amount of the compounds (E)-2-hexenal, (Z)-2-hexen-1-ol, 1-penten-3-ol, hexanal, (Z)-2-penten-1-ol and (E)-2-pentenal, compared to fruits of a similar ripening stage from an isogenic pepper plant not comprising said QTL.

A higher amount is defined herein as the volatile compound abundance, also called intensity, for a specific volatile compound measured on a sample of fruits of plants of the invention carrying the QTL of the invention, or the average volatile compound abundance for a specific volatile compound measured on samples of fruits of plants of the invention carrying the QTL of the invention, being, in order of increased preference, at least 1.2 times higher, 1.5 times higher, 2.0 times higher, 5 times higher, 10 times higher, 15 times higher, than the volatile compound abundance for fruits of a similar ripening stage from an isogenic pepper plant not comprising said QTL included in the same experiment.

Suitably the volatile compound abundance for a specific volatile compound measured on a sample of fruits of plants of the invention carrying the QTL of the invention is at maximum 500 times higher than the volatile compound abundance for fruits of a similar ripening stage from an isogenic pepper plant not comprising said QTL included in the same GC-MS experiment. This corresponds to an increase of, in order of increased preference, at least 0.26 times, at least 0.58 times, at least 1.0 times, at least 1.32 times, at least 2.32 times, at least 3.32 times, at least 3.91 times, and at maximum 8.97 times when peak intensity values are given as log 2 transformed peak intensity values.

A lower amount is defined herein as the volatile compound abundance, also called intensity, for a specific volatile compound measured on a sample of fruits of plants of the invention carrying the QTL of the invention, or the average volatile compound abundance for a specific volatile compound measured on samples of fruits of plants of the invention carrying the QTL of the invention, being, in order of increased preference, at least 1.2 times lower, 1.5 times lower, 2.0 times lower, 3.0 times lower, 5 times lower, 7.5 times lower, 15 times lower, than the average peak intensity for fruits of a similar ripening stage from an isogenic pepper plant not comprising said QTL included in the same experiment. Suitably the volatile compound abundance for a specific volatile compound measured on a sample of fruits of plants of the invention carrying the QTL of the invention is at maximum 500 times lower than the volatile compound abundance for fruits of a similar ripening stage from an isogenic pepper plant not comprising said QTL included in the same GC-MS experiment. This corresponds to a decrease of, in order of increased preference, at least 0.26 times, at least 0.58 times, at least 1.0 times, at least 1.32 times, at least 1.58 times, at least 2.32 times, at least 2.91 times, at least 3.91 times and at maximum 8.97 times when peak intensity values are given as log 2 transformed peak intensity values.

The present invention furthermore covers a pepper plant producing fruits with a novel flavor, caused by a QTL on LG3, and wherein the QTL can be present both homozygously and heterozygously. As pointed out before, the QTL on LG3 has an intermediate effect on the flavor attribute scores aroma, flowers, non-pungent spices, celery, chives, and grassiness for pepper fruits in which the QTL is heterozygously present, compared to pepper fruits with no QTL and pepper fruits with the QTL in a homozygous state. Regarding the effect of the QTL of the invention on the mentioned compounds, the intermediate effect of the heterozygous state of the QTL is not obvious, as it was found that plants with said QTL in heterozygous state had an increased amount of artemisia ketone and/or 6-methyl-4-oxo-5-heptenal and/or (E)-2-hexenal and/or (Z)-2-hexen-1-ol and/or 1-penten-3-ol and/or hexanal and/or (Z)-2-penten-1-ol and/or (E)-2-pentenal and only small decreases in the amount of (Z)-butanoic acid 3-hexenyl ester and 2-isobutyl-3-methoxypyrazine, compared to fruits of a similar ripening stage from an isogenic pepper plant not comprising said QTL.

The invention relates also to seed of pepper plants of the invention and to other parts of the plant that are suitable for sexual reproduction. Such plant parts can be selected from the group consisting of microspores, pollen, ovaries, ovules, embryo sacs and egg cells.

Additionally, the invention also relates to parts of the pepper plants of the invention that are suitable for vegetative reproduction, for example tissue culture, cuttings, roots, stems, cells and protoplasts. Tissue culture can be grown from leaves, pollen embryos, cotyledon, hypocotyls, meristematic cells, roots, anthers, flowers, seeds and stems.

The invention further relates to seed of a pepper plant producing fruits with a novel flavor, wherein the genome of the pepper seed may comprise a QTL, that in the fruits of the plant that can be grown from the seed causes the trait of the novel flavor. In such seed the QTL may be homozygously or heterozygously present, but is preferably homozygously present.

The invention also relates to seed that is capable of growing into a pepper plant of the invention, wherein the genome of the pepper seed may comprise a QTL, that in the fruits of the plant that can be grown from the seed causes the trait of the novel flavor. In such seed the QTL may be homozygously or heterozygously present, but is preferably homozygously present.

The invention furthermore relates to hybrid seed and to a method of producing hybrid seeds which may comprise crossing a first parent plant with a second parent plant and harvesting the resulting hybrid seed. Such hybrid seed may either comprise the QTL of the invention heterozygously or homozygously. In order for all the hybrid seed to carry the trait of the invention homozygously, both parents need to be homozygous for the QTL causing the trait of novel flavor. Both parents thus carry the QTL of the invention. They need not necessarily be uniform for other traits.

Beside the seed of a pepper plant, the invention also covers the progeny derived from a pepper plant producing fruits with a novel flavor. Such progeny may be produced by sexual and vegetative reproduction of a plant of the invention or a progeny plant thereof. The progeny carries the QTL on LG3 as found in the plant of the invention and as present in plants grown from seed which was deposited at the NCIMB under number NCIMB 42137. The said QTL may be present in the progeny both homozygously or heterozygously, preferably the first option. In addition to this, the plant may be modified in one or more other characteristics. Such additional modifications are for example effected by crossing and selecting, mutagenesis or by transformation with a transgene.

As used herein the word "progeny" is intended to mean the offspring or the first and all further descendants from a cross with a plant of the invention that shows the trait of the invention and carries the QTL of the invention underlying the flavor trait. Progeny of the invention may comprise descendants of any cross with a plant of the invention that carries the QTL causing the flavor trait of the invention. Such progeny is for example obtainable by crossing a first pepper plant with a second pepper plant, wherein one of the plants was grown from seeds of which a representative sample was deposited under accession number NCIMB 42137, but may also be the progeny of any other pepper plant carrying the QTL of the invention as present in NCIMB 42137.

Furthermore, the current invention also covers progeny of a pepper plant of the current invention or progeny of pepper plants grown from seeds derived from plants of the current invention, wherein the progeny of the plant may comprise the QTL and wherein the QTL is preferably present in a homozygous state, although the QTL may be present in heterozygous state. The novel flavor trait thus has a genetic basis in the genome of a *Capsicum annuum* plant, and for example by using the sensory analysis described in Example 3 and/or the biochemical analysis as described in Example 4 *Capsicum annuum* plants may be identified as being plants of the invention.

A pepper plant of the invention, producing fruits with a novel flavor that is caused by a QTL on LG3, is obtainable by crossing a first pepper plant not having the QTL, with a second pepper plant having the QTL, or by introgression of the QTL into the first pepper plant from the second pepper plant, and selecting plants that produce fruits which have the said QTL and/or the novel flavor and/or higher amount of the compounds artemisia ketone and/or a higher amount of 6-methyl-4-oxo-5-heptenal and/or a higher amount of (E)-2-hexenal and/or a higher amount of (Z)-2-hexen-1-ol and/or a higher amount of 1-penten-3-ol and/or a higher amount of hexanal and/or a higher amount of (Z)-2-penten-1-ol and/or a higher amount of (E)-2-pentenal and/or a lower amount of (Z)-butanoic acid 3-hexenyl ester and/or a lower amount of 2-isobutyl-3-methoxypyrazine compared to fruits of a similar ripening stage from an isogenic pepper plant not comprising said QTL.

Propagation material derived from a pepper plant of the invention or from pepper seeds from a pepper plant of the invention, is also included in the present invention, wherein the propagation material may comprise the QTL that causes the novel flavor, and the QTL is preferably present in a homozygous state.

The invention also refers to propagation material capable of growing into a pepper plant of the invention, wherein the propagation material may comprise the QTL that causes the novel flavor, and the QTL is preferably present in a homozygous state.

The said propagation material, derived from the pepper plant of the invention as well as propagation material capable of growing into a plant of the invention is for example selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof.

The invention further relates to a cell of a pepper plant of the invention, which cell may comprise the QTL which confers the novel flavor trait, wherein said QTL is present in the genome of a pepper plant grown from seeds of which a representative sample was deposited with the NCIMB under accession number NCIMB 42137. Said pepper plant is obtainable by crossing a pepper plant with a second pepper plant, in particular a pepper plant grown from seed as deposited under accession number NCIMB 42137, and selecting for a pepper plant that has the flavor trait of the invention. The said cell thus may comprise the genetic information which is substantially identical, preferably completely identical to the genetic information encoding the said novel flavor trait of the pepper plant grown from seeds of which a representative sample was deposited under NCIMB accession number 42137, more in particular the QTL described herein. Preferably, the cell of the invention is a part of a plant or plant part, but the cell may also be in isolated form.

In one embodiment, the invention relates to the use of seeds with NCIMB accession number NCIMB 42137, for transferring the QTL of the invention, which confers the flavor trait of the invention, into another pepper plant.

In another embodiment, the invention relates to the use of a pepper plant, which plant carries the QTL of the invention, which confers the flavor trait of the invention, as present in and obtainable from a *Capsicum baccatum* or a pepper plant carrying the QTL of the invention, in particular a pepper plant grown from seed with NCIMB accession number NCIMB 42137, as a crop.

The invention also relates to the use of a pepper plant, which carries the QTL of the invention which confers the flavor trait of the invention, as present in and obtainable from a *Capsicum baccatum* or a pepper plant, in particular a pepper plant grown from seed with NCIMB accession number NCIMB 42137, as a source of seed.

In yet another embodiment, the invention relates to the use of a pepper plant, which carries the QTL which confers the flavor trait of the invention as present in and obtainable from a *Capsicum baccatum* or a pepper plant, in particular a pepper plant grown from seed with NCIMB accession number NCIMB 42137, as a source of propagating material.

Further, the invention relates to the use of a pepper plant, which carries the QTL which confers the flavor trait of the invention, as present in and obtainable from a *Capsicum baccatum* or a pepper plant, in particular a pepper plant grown from seed with NCIMB accession number NCIMB 42137, for consumption.

In another embodiment, the invention relates to the use of a pepper plant or a *Capsicum baccatum* plant, which carries the QTL which confers the flavor trait of the invention as present in seeds with NCIMB accession number NCIMB 42137, for conferring the QTL that leads to the trait of the invention to a pepper plant.

In yet another embodiment, the invention relates to the use of a pepper plant, as a recipient of the QTL as present in and obtainable from a *Capsicum baccatum* or a pepper plant carrying the QTL of the invention, in particular a pepper plant grown from seed with NCIMB accession number NCIMB 42137.

The current invention also relates to a pepper fruit, or parts thereof, harvested from a pepper plant of the invention, producing fruits with a novel flavor and which may comprise the QTL as defined herein. Naturally this also relates to any food product or processed food product made of said pepper fruit.

The processed pepper fruit may also be included in another food product, such as sauce, pie, soup or a dried or fresh pasta product, such as ravioli, tortellini, cannelloni etc. Such food product will usually be pre-packed and is intended for sale in a supermarket. The invention thus also relates to the use of pepper fruits harvested from a pepper plant of the invention, or parts thereof, in the preparation of food products, in particular sauces, salads, pies, soups and pastas.

A pepper plant of the invention could also be used as germplasm in a breeding program for the development of other pepper plants that may comprise the QTL that causes the novel flavor. This kind of use is also covered by the current invention.

Moreover, the invention relates to a nucleic acid or a part thereof, optionally in isolated form, which causes novel flavor in pepper fruits, which nucleic acid originates from LG3 and is linked thereon to at least one molecular marker selected from the group consisting of SEQ ID No:1, SEQ ID No:3, SEQ ID No:5, SEQ ID No:7, SEQ ID No:9 and SEQ ID No:11 and/or is present in seeds with NCIMB accession number NCIMB 42137. A person skilled in the art would be able to isolate the nucleic acid causing the flavor trait of the invention or a part thereof from the genome of a pepper plant of the invention, and use it to create new molecular markers that are linked with the QTL and with the trait of the invention.

The present invention also relates to the use of a molecular marker, wherein the marker is selected from the group consisting of SEQ ID No:1, SEQ ID No:3, SEQ ID No:5, SEQ ID No:7, SEQ ID No:9 and SEQ ID No:11 to identify the QTL located on LG3 in a pepper plant with a novel flavor, or to develop a pepper plant with novel flavor.

The present invention further relates to the use of said molecular marker to identify or develop other markers linked to the QTL on LG3 that causes the novel flavor.

In order to establish the presence of the QTL of the invention in the genome of a seed or plant at least one molecular marker is necessary but any combination of the molecular markers according to SEQ ID No:1, SEQ ID No:3, SEQ ID No:5, SEQ ID No:7, SEQ ID No:9 and SEQ ID No:11 may be used. Genotyping a population or collection of plants that is not uniform for the flavor trait of the invention can be done using at least one molecular marker set selected from the group consisting of SEQ ID No:1 plus SEQ ID No:2, SEQ ID No:3 plus SEQ ID No:4, SEQ ID No:5 plus SEQ ID No:6, SEQ ID No:7 plus SEQ ID No:8, SEQ ID No:9 plus SEQ ID No:10 and SEQ ID No:11 plus SEQ ID No:12. The presence of the flavor trait of the invention can also be determined phenotypically in either generation of an introgression process.

In one aspect the invention relates to a method for production of a pepper plant which has the trait of novel flavor, which may comprise
a) crossing a plant which may comprise a QTL that leads to the trait with another plant;
b) selecting plants that have the trait in the next generation;
c) optionally performing one or more additional rounds of selfing or crossing, and subsequently selecting, for a plant which may comprise/show the trait of the invention.

Selecting plants that have the trait of novel flavor can be done molecularly using molecular markers linked to the trait as described herein and/or phenotypically in the F1 or F2 or any further generation.

The word "trait" in the context of this application refers to the phenotype of the plant. In particular, the word "trait" refers to the trait of the invention, more in particular to the trait of pepper fruits with novel flavor. The term "QTL" (i.e. "quantitative trait locus") is used for the genetic information in the genome of the plant that causes the flavor trait of the invention. When a plant shows the flavor trait of the invention, its genome may comprise the QTL causing the trait of the invention. The plant thus has the QTL of the invention. In the present invention the QTL is an introgression from *C. baccatum* on Linkage Group 3 (LG3).

It is clear that the parent that provides the trait of the invention is not necessarily a plant grown directly from the deposited seeds. The parent may also be a progeny plant from the deposited seed, obtained by for example selfing or crossing, or a progeny plant from seeds that are identified to have the trait of the invention by other means.

In one aspect, the invention relates to a method for production of a pepper plant which has the trait of novel flavor, which may comprise
a) crossing a plant which may comprise the QTL that leads to the trait with another plant;
b) optionally backcrossing the resulting F1 with the preferred parent;
c) selecting for plants that have the trait in the next generation;
d) optionally performing one or more additional rounds of selfing or crossing, and subsequently selecting, for a plant which may comprise the trait.

The invention additionally provides a method of introducing another desired trait into a pepper plant which has the trait of novel flavor, which may comprise:
a) crossing a pepper plant that has the trait of novel flavor, representative seeds of which were deposited under deposit number NCIMB 42137, with a second pepper plant that may comprise a desired trait to produce F1 progeny;
b) selecting in the F1 progeny plants that comprise said trait of novel flavor and the desired trait;
c) crossing the selected F1 progeny plants with either parent, to produce backcross progeny;
d) selecting backcross progeny plants which may comprise the desired trait and the trait of novel flavor; and
e) optionally repeating steps c) and d) one or more times in succession to produce selected fourth or higher backcross progeny that may comprise the desired trait and the trait of novel flavor. The invention includes a pepper plant produced by this method.

In one embodiment selection for plants having the trait of novel flavor is done in the F1 or any further generation by using any or any combination of the markers according to SEQ ID No:1, SEQ ID No:3, SEQ ID No:5, SEQ ID No:7, SEQ ID No:9 and SEQ ID No:11. In another aspect, selection for the trait of the invention is started in the F2 of a cross or alternatively of a backcross. Selection of plants in the F2 can be done phenotypically as well as by using the said marker(s) which directly or indirectly detect(s) the QTL underlying the trait. Phenotypic selection can suitably be done by tasting and/or by determining the biochemical profile of the pepper fruits.

In one embodiment selection for plants having the trait of novel flavor is started in the F3 or a later generation.

In one embodiment the plant which may comprise the QTL is a plant of an inbred line, a hybrid, a doubled haploid, or of a segregating population.

The invention further provides a method for the production of a pepper plant having the trait of novel flavor by using a doubled haploid generation technique to generate a doubled haploid line which may comprise said trait.

The invention furthermore relates to hybrid seed that can be grown into a plant having the trait of novel flavor and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid pepper plant that has the trait of novel flavor, which may comprise crossing a first parent pepper plant with a second parent pepper plant and harvesting the resultant hybrid seed, of which the first parent plant and/or the second parent plant has the trait of novel flavor, and growing said hybrid seeds into hybrid plants having the trait of novel flavor.

The invention also relates to a method for the production of a pepper plant having the trait of novel flavor by using a seed that may comprise a QTL in its genome that leads to the trait of novel flavor for growing the said pepper plant. The seeds are suitably seeds of which a representative sample was deposited with the NCIMB under deposit number NCIMB 42137.

The invention also relates to a method for seed production which may comprise growing pepper plants from seeds of which a representative sample was deposited with the NCIMB under deposit number NCIMB 42137, allowing the plants to produce seeds, and harvesting those seeds. Production of the seeds is suitably done by crossing or selfing.

In one embodiment, the invention relates to a method for the production of a pepper plant having the trait of novel flavor by using tissue culture.

The invention furthermore relates to a method for the production of a pepper plant having the trait of novel flavor by using vegetative reproduction.

In one embodiment, the invention relates to a method for the production of a pepper plant having the trait of novel flavor by using a method for genetic modification to introgress the QTL causing the said trait into the pepper plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

In one embodiment, the source from which the genetic information is acquired, in particular the QTL, is formed by a plant grown from the deposited seeds, or by sexual or vegetative descendants thereof.

In another embodiment, the source from which the genetic information is acquired, in particular the QTL, is formed by a *Capsicum baccatum* plant.

The invention also relates to a breeding method for the development of pepper plants that have the trait of novel flavor wherein germplasm which may comprise the QTL causing said trait is used. The germplasm is constituted by all inherited characteristics of an organism and according to the invention encompasses at least the novel flavor trait of the invention. Representative seed of said plant which may comprise the QTL and being representative for the germplasm was deposited with the NCIMB under deposit number NCIMB 42137.

In a further embodiment the invention relates to a method for the production of a pepper plant having the trait of novel flavor wherein progeny or propagation material of a plant which may comprise the QTL conferring said trait is used as a source to introgress the said trait into another pepper plant. Representative seed of said plant which may comprise the QTL was deposited with the NCIMB under deposit number NCIMB 42137.

Furthermore, the invention relates to a novel flavor gene that leads to a pepper plant having the novel flavor trait of the invention, and which novel flavor gene is as present in the genome of plants of which a representative sample was deposited with the NCIMB under deposit number NCIMB 42137. The skilled breeder knows how to use such plant as a source of the novel flavor gene for introgressing the novel flavor gene into a plant.

The invention also relates to the use of the QTL that leads to a pepper plant producing fruits having the trait of novel flavor, for producing a plant which has the trait of novel flavor, in particular a pepper plant which has the novel flavor trait, which QTL is as present in the genome of plants of which a representative sample was deposited under deposit number NCIMB 42137.

According to another aspect thereof the invention relates to a non-naturally occurring plant producing fruits having a novel flavor, and which novel flavor is the result of the presence in the genome of the plant of the QTL which is as present in the genome of plants of which a representative sample was deposited under deposit accession number 42137. The non-naturally occurring plant is in particular a mutant plant.

Introgression as used in this application is intended to mean introduction of a trait into a plant not carrying the trait by means of crossing and selecting.

The term 'nucleic acid' is used for a macromolecule, a DNA or RNA molecule, the genetic information that causes the trait of the invention. When a plant shows the phenotypic trait of the invention, its genome may comprise the nucleic acid causing that trait. The plant thus has the nucleic acid of the invention. In the present invention the nucleic acid is part of the QTL introgressed from *C. baccatum* on Linkage Group 3 (LG3).

The invention provides preferably a pepper plant having the trait of novel flavor, which plant is obtainable by any of the methods described herein and/or familiar to the skilled person.

In the absence of molecular markers, or in the instance that recombination between the QTL and the marker has taken place so that the marker is not predictive anymore, it can be determined by an allelism test whether the trait is caused by the same QTL. To perform an allelism test, a tester plant which is homozygous for the known QTL of the invention is crossed with material to be tested that is also homozygous for the genetic information underlying the flavor trait. When no segregation for the trait to be observed is present in the F2 of the cross, the QTLs have been proven to be equivalent or the same.

When more than one gene may be responsible for a certain trait, and an allelism test is done to determine equivalence, the skilled person doing the test has to make sure that all relevant genes are present homozygously for the test to work properly.

TABLE 1

Molecular SNP markers

| marker name | L G | position (cM) | Sequence marker |
|---|---|---|---|
| SEQ ID No: 1 | 3 | 32.93 | GAGTGGCAGTGATTT TTTCTGATAGCAACA ACGCACCTATTGAGA GATTTGTTTTCAAGA TAAATGTGAACCAGT CCTATGGTTCGAAGT TGGAGG |
| SEQ ID No: 2 | 3 | 32.93 | GAGTGGCAGTGATTT TTTCTGATAGCAACA ACGCACCTATTGAGA GATTTATTTTCAAGA TAAATGTGAACCAGT CCTATGGTTCGAAGT TGGAGG |
| SEQ ID No: 3 | 3 | 33.28 | GGGATGAAAGAAAAG CTAGATTCTAGAAAA TTGGTGATGGGAAAC ATGTCAATGCATTCT AAAGTAGTCAAAGAG AAAGTCAAGAAGCAA GAGGAGCAACT |
| SEQ ID No: 4 | 3 | 33.28 | GGGATGAAAGAAAAG CTAGATTCTAGAAAA TTGGTGATGGGAAAC ATGTCAGTGCATTCT AAAGTAGTCAAAGAG AAAGTCAAGAAGCAA GAGGAGCAACT |
| SEQ ID No: 5 | 3 | 33.28 | CACTTCTCAAATGCT TAAAGGCCATTAGAG ACCACGCTTTTGTTA AGTCGCCTTATCCTG TCATAATCACGTTGG AAGACCACTTGACAC CAGATCTTC |
| SEQ ID No: 6 | 3 | 33.28 | CACTTCTCAAATGCT TAAAGGCCATTAGAG ACCACGCTTTTGTTA AGTCGTCTTATCCTG TCATAATCACGTTGG AAGACCACTTGACAC CAGATCTTC |
| SEQ ID No: 7 | 3 | 33.32 | CATTATAACACATCC AGTATACAAAATAAA CACTCCCAGATTTAG AGTAACCAAATTTCC AAAACAATACCGAAA GCC |
| SEQ ID No: 8 | 3 | 33.32 | CATTATAACACATCC AGTATACAAAATAAG CACTCCCAGATTTAG AGTAACCAAATTTCC AAAACAATACCGAAA GCC |
| SEQ ID No: 9 | 3 | 33.40 | CGCCTAAGCGCACAC ACAAGTGTACGTGGT CTACCAAGTATTWAA ACCTTTCAACCTCAC TTGAGGCCTTATACT TCACTTTATATATCC ACCTGCAACCAATAG CCTTCTTTCCTTTAG GTAGAGCAACAATCT CCCAAGTATGATTGG AATTCAAGGC |
| SEQ ID No: 10 | 3 | 33.40 | CGCCTAAGCGCACAC ACAAGTGTACGTGGT CTACCAAGTATTWAA ACCTTTCAACCTCAC TTGAGGCCTTATACT TCACTTTATATATCC ACCTGCAACCAATAG CTTTCTTTCCTTTAG GTAGAGCAACAATCT CCCAAGTATGATTGG AATTCAAGGC |
| SEQ ID No: 11 | 3 | 33.41 | GGAGAAGCTTGGTCC TCAACTCGCCATTAT TGCTCCGATCAAGTA CTGAGGTCGAAATAT AGTTTGTTTCAAGTA AAATTTTGATGGAGG TTGATGTTTTGGCAT TAGTG |
| SEQ ID No: 12 | 3 | 33.41 | GGAGAAGCTTGGTCC TCAACTCGCCATTAT TGCTCCGATCAAGTA CTGAGGTCGAAGTAT AGTTTGTTTCAAGTA AAATTTTGATGGAGG TTGATGTTTTGGCAT TAGTG |

The SNP sequences of the markers SEQ ID No:1, SEQ ID No:3, SEQ ID No:5, SEQ ID No:7, SEQ ID No:9 and SEQ ID No:11 are in the genome of seeds of the deposit NCIMB 42137 linked to the QTL of the invention, which confers the novel flavor to fruits of pepper plants. These SNP sequences can be used as molecular markers for novel flavor of fruits of plants grown from seeds from said deposit.

The sequences of SEQ ID No:2, SEQ ID No:4, SEQ ID No:6, SEQ ID No:8, SEQ ID No:10 and SEQ ID No:12 represent the wildtype *C. annuum* alleles for the molecular SNP markers SEQ ID No:1, SEQ ID No:3, SEQ ID No:5, SEQ ID No:7, SEQ ID No:9 and SEQ ID No:11, respectively.

The nucleotides that differ between the marker and the wildtype are underlined.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Development of a Pepper Plant with a New Flavor

The *Capsicum baccatum* var. *pendulum* accession PEN45 was used as donor parent for backcrossing (BC) with three cultivated *Capsicum annuum* blocky breeding lines (MT, SM and GNM). Because of difficulties in interspecific crossing, a multi-parent $BC_2$ population, consisting of three sub-populations, was generated for linkage map development. The largest PEN45 $BC_2$ sub-population out of the three, with the blocky parents SM and GNM in its pedigree, was chosen to study fruit characteristics in more detail. In this population 34 of the in total 54 $BC_2$ plants gave sufficient inbred seeds to grow $BC_2S_1$ lines. In 2009 the 34 $BC_2S_1$ lines were grown in plots of 5-9 plants with, if possible, 2 repetitions (possible for 23 $BC_2S_1$ lines) in a randomized block design. Plants were grown in soil in a greenhouse in De Lier, The Netherlands, with 2 stems per plant and with 2.5 plants/$m^2$.

Due to the generation ($BC_2S_1$) of the material and the presence of two different breeding lines (SM and GNM) in their pedigree, the lines were still segregating for several traits. To grow the $BC_2S_1$ lines as uniformly as possible, plants were pre-selected with a marker based on the Pun1 locus for non-pungent plants and with a marker based on the CCS gene (capsanthin-capsorubin synthase) for non-red (i.e. yellow or orange) plants. To compensate for selection against Pun1 or CCS linked PEN45 fragments with potentially interesting characteristics, two and five $BC_2S_1$ lines (out of the 34 lines) were used to select plants with homozygous pungent orange fruits and homozygous non-pungent red fruits, respectively. These plants were also grown in 2 repetitions with plots of 5 plants. Genotypes SM, GNM and PEN45 were grown as controls in four repetitions.

At the time of maturation of the first fruits the BC2S1 plots were made phenotypically more uniform by removing the most aberrant, mainly sterile, plants from the plots. In total 25 of the $BC_2S_1$ lines were uniform for orange color, the other 9 lines were segregating for plants with either orange or yellow fruits. In the end 250 $BC_2S_1$ plants remained in 69 plots (1-6 plants) and were used for QTL mapping, of which 160 orange, 61 yellow and 29 red fruited plants.

Three different $BC_2S_1$ plants, derived from three different $BC_2$ plants, were used to develop near-isogenic lines (NILs) by one generation of backcrossing with GNM followed by two selfing steps. A NIL population consists of genetically homogeneous lines, which only differ from each other by the presence of (different) single or only a limited number of introgression fragments from a donor parent. In this case, the donor parent is the accession PEN45, the *C. baccatum* parent.

Each generation (i.e. resulting from both backcrossing and selfing steps) was genotyped with SNPs flanking the original $BC_2S_1$ introgressions to obtain lines with a limited number of introgressions in a GNM genetic background. In 2011 23 NILs and the recurrent parent (GNM) were grown in three repetitions with 5 plants per plot in a completely randomized setup. Plants were grown under similar conditions as the $BC_2S_1$ lines in a greenhouse, this time in autumn and on rockwool.

Example 2

Sampling of Pepper Fruits for Sensory and Biochemical Analysis

Ripe (95-100% colored) pepper fruits from the second fruit set were used for biochemical measurements and sensory evaluation. Fruits were stored after harvesting in a climate room at 20° C. with 80% relative humidity for 3-4 days to optimize ripening. This is a procedure to mimic the Dutch commercial system. During the day of the sensory evaluations, fruits were washed with cold running tap water, dried with a clean towel, cut (top and bottom parts were discarded) in 1-2 cm pieces, these pieces were mixed and seeds were removed. Half of the fruit pieces from each sample were immediately frozen in liquid nitrogen, ground in an electric mill and stored at −80° C. for later biochemical analysis, while the other half was used for flavor evaluation.

Fruits of the BC2S1 plants were harvested per plot and in case of plots segregating for plants with either orange or yellow fruits, the two colors were bulked separately. 56 BC2S1 plots (37 orange, 15 yellow and 4 red) gave sufficient fruits to make representative fruit samples of 5-8 fruits for sensory evaluation. In addition 32 samples were made up of plots and/or individual plants that did not give enough fruits for sensory evaluation or that were pungent.

In the NIL experiment, 20 NILs and GNM gave sufficient fruits and were evaluated as bulks per plot.

Example 3

Sensory Analysis

The descriptive analysis of the trait of the invention took place in a sensory laboratory at Wageningen UR Greenhouse Horticulture (WUR-GH, Bleiswijk, The Netherlands). Thirteen independent panelists, who are part of a trained panel with broad experience in sensory evaluations of food products, including pepper, took part in the experiment.

Two different experiments were done. In 2009 the 34 BC2S1 lines were tested and in 2011 the NILs, derived from these BC2S1 lines were tested.

In both experiments each panelist received 5 fruit pieces per sample in a ceramic cup and they were asked to mark the intensity of the attributes on a horizontal 100-mm structured line scale on paper, resulting in a scoring between 0 and 100. The pepper fruit pieces were swallowed by the panelists. Between samples, panelists rinsed their mouth with tasteless mineral water to neutralize their palate and were also allowed to eat a small unsalted cracker before rinsing their mouth. No information was provided to the panel about the genotypes.

In the BC2S1 experiment, in the weeks prior to the test sessions, panelists participated in training sessions with commercially available pepper genotypes. During the training sessions, panelists agreed on fourteen attributes to describe the flavor sensation in the mouth, which were the texture attributes crunchiness, stickiness of the skin, toughness and juiciness, the basic taste attributes sweetness and sourness and the retronasal flavor attributes aroma intensity, grassiness, green bean, carrot, fruity/apple, perfume, petrochemical and musty. In neither experiment the panel separately evaluated the odor (nasal) of the fruits. During the BC2S1 experiment test sessions, each panelist evaluated 21-22 genotypes in a randomized order, split over 2 subsequent days. On both days, 2 sessions with 5-6 genotypes were evaluated per panelist. In this setup each sample was evaluated by 4-5 panelists.

In the weeks prior to the test sessions for the NIL experiment, panelists participated in training sessions with fruits from preselected NILs with divergent flavors.

For the ML experiment twelve panelists were divided in three groups of four persons. Each group evaluated the 20 NILs of a single repetition in a randomized order (complete block design), divided over 2 subsequent days. On both days, 2 sessions with 5 NILs and GNM as the reference were evaluated per panelist.

During the sensory evaluation of the fruits in the BC2S1 experiment it became clear that the vocabulary (i.e. the predefined attributes) of the trained panel was not sufficient to cover all the flavor variation, which resulted in remarks on the evaluation sheets like 'presence of tropical fruit flavor', 'chives flavor' or 'similar to papaya'. This was caused by the fact that the panelists participated in training sessions with only commercially available genotypes, lacking these novel and unexpected flavors. For the NIL experiment the test panel was therefore also trained with fruits from preselected NILs having more extreme flavors than currently available in the Dutch commercial pepper segment. This resulted in an expansion of the panel's vocabulary with the flavor attributes flowers, non-pungent spices, celery, chives and bitter, while the attribute perfume was no longer used.

The sensory data was analysed in Genstat version 12 using a linear mixed model REML (residual maximum likelihood) analysis. For the BC2S1 experiment a model was used with genotype, replicate and their interaction as fixed terms. Sessions (tasting sessions) within replicate/genotype combinations and panelists within sessions were taken as random terms. In the statistical analysis of the NIL experiment a model was used with genotype as fixed term. Panelist, the panelist/genotype interaction and repetitions within panelist/genotype combinations were taken as random terms. In this experiment repetition and session were completely confounded with panelist and therefore not corrected for as a combined factor.

In order to obtain an odor intensity evaluation (nasal), mature fruits of the $BC_2S_1$ plants were harvested and pooled per plot (76 samples excluding controls). Five representative fruits per sample were cut and evaluated for odor (nasal) intensity (scale: 0=no odor–7=a lot of odor, like C. baccatum accession PEN45) by three persons.

QTL analysis using the sensory data was performed as described in Example 5.

Interestingly, a rather strong QTL (LOD 7.97, 38.7% explained variance) for odor intensity, was found on LG3 at 33.3 cM, with the C. baccatum allele giving a more intense odor than the C. annuum allele (increase of 3 points on 0-7 scale). Nomenclature of linkage groups is referred to the consensus chromosome numbers as in Wu et al. (Theor. Appl. Genet. (2009) 118, 1279-1293).

Analysis of the sensory data from the NIL experiment using the non-parametric Kruskal-Wallis test, showed that NILs having either a heterozygous (NIL40, NIL46 and NIL48) or homozygous (NIL37, NIL38 and NIL39) LG3 C. baccatum introgression from 32.9 to 33.4 cM (FIG. 2) have significantly higher scores for the retronasal flavor attributes aroma, flowers, non-pungent spices, celery and chives, and a significantly lower score for the retronasal flavor attribute grassiness (Table 2). This confirmed that the small C. baccatum introgression on LG3 from 32.9 to 33.4 cM has an extraordinary effect on flavor.

The said effects were strongest in the fruits of plants that had the QTL on LG3 in a homozygous state. In the fruits of plants that had the QTL on LG3 in a heterozygous state, the scores for flavor attributes aroma, flowers, non-pungent spices, celery, chives and grassiness were intermediate between those of pepper fruits of plants without the QTL of the invention and fruits of plants that had the QTL of the invention in a homozygous state.

The flavor of the fruits of the C. baccatum var. pendulum parent line was tested separately by a group of persons accustomed to eat pungent food. This group described the taste of the fruits of the C. baccatum var. pendulum parent line as fruity, not very aromatic and sour. This is in clear contrast with the much larger variation in flavors found in plants of the invention, and makes the effect the introgression of C. baccatum has in plants of the invention very unexpected.

TABLE 2

LG3 volatile and flavor QTL scores

| | BC$_2$S$_1$ population | | | | | | | | NILs | | | | |
|---|---|---|---|---|---|---|---|---|---|---|---|---|---|
| Compound/attribute | LOD | %EV | μA | μH | μB | Add. | GNM | OG | Signif. | mA | mH | mB | A/H/B |
| Aroma | na | na | na | na | na | na | na | na | 0.0001 | 51.4 | 60.8 | 68.1 | 45/9/9 |
| Grassiness | na | na | na | na | na | na | na | na | 0.01 | 10.6 | 5.2 | 5.2 | 45/9/9 |
| Flowers | na | na | na | na | na | na | na | na | 0.01 | 3.8 | 7.8 | 8.9 | 45/9/9 |
| Spices (non-pungent) | na | na | na | na | na | na | na | na | 0.005 | 7.0 | 13.7 | 15.2 | 45/9/9 |
| Celery | na | na | na | na | na | na | na | na | 0.0001 | 2.2 | 6.3 | 8.9 | 45/9/9 |
| Chives | na | na | na | na | na | na | na | na | 0.0001 | 1.4 | 6.6 | 10.5 | 45/9/9 |
| 4-Mercapto-4-methyl-2-pentanone | 4.3 | 20.3 | 11.9 | 13.8 | 15.7 | -1.89 | 8.3 | 8.6 | — | nd | nd | nd | nd |
| Artemisia ketone or 6-Methyl-4-oxo-5-heptenal | 16.1 | 56.9 | 9.3 | 13.3 | 17.2 | -3.96 | 8.9 | 8.8 | 0.0001 | 10.3 | 15.0 | 14.0 | 45/9/9 |
| (Z)-Butanoic acid 3-hexenyl ester | 3.9 | 18.3 | 14.6 | 13.0 | 11.3 | 1.68 | 14.4 | 15.8 | 0.0001 | 14.1 | 13.9 | 12.0 | 45/9/9 |
| 2-Isobutyl-3-methoxypyrazine | 3.2 | 15.5 | 18.6 | 17.8 | 17.1 | 0.78 | 17.9 | 19.5 | 0.0001 | 17.8 | 17.6 | 16.0 | 45/9/9 |
| (E)-3,6-dihydroxy-2-methyl-1,4-benzoquinone-4-methoxyimine-N-oxide | 21.7 | 67.8 | 8.7 | 11.7 | 14.6 | -2.94 | 8.6 | 8.4 | — | nd | nd | nd | nd |

LG3 refers to the C. baccatum introgression of 32.9-33.4 cM from linkage group 3. Percentage of explained variance (% EV), estimated (μ, Van Ooijen, MapQTL 6: software for the mapping of quantitative trait loci in experimental populations of diploid species (2009) Kyazma BV, Wageningen) or direct means (m), estimated additive effect (add.) and genotype distribution (A/H/B) are given. A=homozygous for WT C. annuum allele, H=heterozygous, B=homozygous for the LG3 C. baccatum introgression. For the $BC_2S_1$ population experiment, the average metabolite values for GNM (C. annuum parent) fruits and for OG (Orange Glory, a commercially available orange blocky type C. annuum variety) fruits are included. Metabolite values represent log 2 values of peak intensities. na=not available, nd=not detected.

Example 4

Metabolic Profiling

The biochemical profiling of both the BC2S1 and the NILs experiments was performed as described in Eggink et al. (Food Chemistry (2012) 132, 301-310). In the BC2S1 experiment 92 pepper fruit samples were analyzed, among which samples of fruits of the C. annuum parent line GNM and samples of fruits of the commercial orange blocky C. annuum hybrid reference line Orange Glory.

In short, the profiling of volatile metabolites was performed using headspace SPME-GC-MS. Derived GC-MS profiles were processed by the MetAlign™ software package (http://www.metalign.nl) for baseline correction, noise estimation and ion-wise mass spectral alignment. The Multivariate Mass Spectral Reconstruction (MMSR) approach (Tikunov et al., Metabolomics (2012) 8, 714-718) was used to reduce data to volatile compound mass spectra. Each compound was represented by a single selective ion fragment in the following multivariate data analysis. The compounds (number of fragment ions in a mass spectrum ≥5) were then subjected to a tentative identification using the NIST mass spectral library (http://www.nist.gov). Reliable identities were assigned to compounds with a mass spectra match factor ≥600. Volatile compound abundance (intensity) is represented as the height of a selective mass peak of a compound detected in chromatograms by MetAlign software. Intensities which were below the detection limit in certain genotypes, obtained a random value between 250 and 500.

In the BC2S1 experiment in total 222 putative volatile compounds were detected, of which 22 volatiles were specific to PEN45 (i.e. under detection limit in all BC2S1 plants and *C. annuum* parents). Putative identities could be assigned to 178 of these. In the NIL experiment in total 137 putative volatile compounds were detected. Identities were assigned to 96 of these.

After the confirmation that the small *C. baccatum* introgression on LG3 has an extraordinary effect on flavor (see a.o. Example 3), it was checked for which metabolites QTLs could be mapped, as described in Example 5, to the LG3 region in the BC2S1 population. This resulted in five volatiles (Table 2). From these five metabolites three were also detected and confirmed in the NILs. The peak that represents either artemisia ketone or 6-methyl-4-oxo-5-heptenal showed a strong increase in intensity in the presence of the *C. baccatum* allele, while the compounds (Z)-butanoic acid 3-hexenyl ester and 2-isobutyl-3-methoxypyrazine were decreased in NILs having the introgression (Table 2).

The confirmed up-regulated compounds were also checked for their direct relation to odor in the BC2S1 population, resulting in a correlation of 0.53 for the peak that represents either artemisia ketone or 6-methyl-4-oxo-5-heptenal. The intensity of the two down-regulated compounds, (Z)-butanoic acid 3-hexenyl ester and 2-isobutyl-3-methoxypyrazine, was only decreased in the homozygous NILs and not in the heterozygous NILs, while the concentrations of the compound that can be either artemisia ketone or 6-methyl-4-oxo-5-heptenal are even slightly higher in the heterozygous versus the homozygous NILs (Table 2). An effect of 2-isobutyl-3-methoxypyrazine alone on aroma was not found, as NILs with a significantly decreased or increased intensity were unaffected for aroma intensity.

In a follow-up experiment homozygous sub-NILs were selected having the LG3 QTL and compared to sub-NILs without the LG3 QTL. From each plant line a plot with 5 plants was grown. Subsequently the presence or absence of the flavor of the invention was scored by tasting the fruits by 2 persons and profiling of volatile metabolites was performed on fruit samples (in general 2 fruits per sample) from individual plants by SPME-GC-MS, as described before. This resulted in a confirmation of the LG3 QTL flavor effect (Table 3). Samples with the LG3 flavor QTL were again lower in 2-isobutyl-3-methoxypyrazine, higher in the compound that is either artemisia ketone or 6-methyl-4-oxo-5-heptenal, and higher in some lipid derived volatiles: (E)-2-hexenal, (Z)-2-hexen-1-ol, 1-penten-3-ol, hexanal, (Z)-2-penten-1-ol and (E)-2-pentenal.

TABLE 3

Flavor and biochemical effects of the QTL of the invention on LG3

| Compound | Signif. | Sub-NILs A | GNM A | Sub-NILs A | Sub-NILs B | GNM B | NIL38 B |
|---|---|---|---|---|---|---|---|
| Artemisia ketone or 6-methyl-4-oxo-5-heptenal | 0.0001 | 8.8 | 8.8 | 8.8 | 13.6 | 14.3 | 14.8 |
| (E)-2-Pentenal | 0.0001 | 12.3 | 12.1 | 11.7 | 13.0 | 13.4 | 12.9 |
| 1-Penten-3-ol | 0.0001 | 15.2 | 15.1 | 14.8 | 16.2 | 16.1 | 15.7 |
| Hexanal | 0.0001 | 18.1 | 17.7 | 16.0 | 19.5 | 19.5 | 19.2 |
| (Z)-2-Penten-1-ol | 0.0001 | 14.5 | 14.3 | 13.7 | 15.3 | 15.6 | 15.4 |
| (E)-2-Hexenal | 0.0001 | 16.2 | 16.0 | 13.8 | 17.3 | 17.3 | 17.1 |
| (Z)-2-Hexen-1-ol | 0.005 | 18.0 | 17.5 | 18.1 | 18.4 | 18.9 | 19.0 |
| 2-Isobutyl-3-methoxypyrazine | 0.005 | 17.8 | 17.4 | 17.9 | 15.7 | 16.9 | 16.5 |
| Flavor of invention[1] | | – | – | – | + | + | + |

The genotypes of the sub-NILs, *C. annuum* parent GNM and NILS18 are indicated as follows: A = homozygous for the wildtype *C. annuum* allele, B = homozygous for the LG3 *C. baccatum* introgression of the invention. Metabolite values represent the average log2 peak intensities from 5 plants.
[1]Absence of flavor of the invention (–), presence of flavor of the invention (+).

Example 5

QTL Analysis

The 250 BC2S1 plants from the PEN45 BC2 sub-population having the blocky parents SM and GNM in its pedigree, were genotyped with 239 SNPs that were polymorphic in PEN45 versus SM and GNM. Interval mapping, with separate sessions for sensory attributes (14 attributes, 56 plots), metabolites (200 volatiles and 6 non-volatiles, 88 plots/plants) and several physical fruit characteristics plus odor (either on 250 plants or 76 plots), allowed identification of QTLs within all trait classes.

The Interval Mapping method within the program MapQTL 6 (Van Ooijen, MapQTL 6: software for the mapping of quantitative trait loci in experimental populations of diploid species (2009) Kyazma BV, Wageningen) was used for QTL identification in the BC2S1 experiment. A permutation test was applied to each data set (1000 permutations) to determine the LOD (Logarithm of odds) thresholds. A genome wide (GW) LOD threshold of 2.7 was used for QTL significance (p<0.05). The chromosomal locations with the highest LOD scores were considered to be the most likely positions of a QTL. Graphics were produced by MapChart software (Voorrips, Journal of Heredity (2002) 93, 77-78). The ML experiment was analyzed using the non-parametric Kruskal-Wallis test within MapQTL 6 to identify markers that showed significant (p<0.05) trait associations. The analyses in both experiments were performed with log 2 transformed metabolite data.

The invention is further described by the following numbered paragraphs:

1. A pepper plant (*Capsicum annuum* L.) that produces fruits with a novel flavor, wherein the pepper plant comprises a QTL which when present leads to the novel flavor, wherein the QTL is located on LG3 and wherein said QTL is the same as a QTL that is present in the genome of plants grown from seeds of deposit NCIMB 42137 and is linked therein to at least one marker selected from the group consisting of SEQ ID No:1, SEQ ID No:3, SEQ ID No:5, SEQ ID No:7, SEQ ID No:9 and SEQ ID No:11, and wherein the QTL is preferably homozygously present.

2. A pepper plant of paragraph 1, wherein the QTL is the same as a QTL that is present in the genome of plants grown from seeds of deposit NCIMB 42137 and is linked therein to markers SEQ ID No:1, SEQ ID No:3, SEQ ID No:5, SEQ ID No:7, SEQ ID No:9 and SEQ ID No:11.

3. A pepper plant of paragraph 1 or 2, wherein the QTL is as present in the genome of, or obtainable from, *Capsicum baccatum* or pepper plants grown from seeds which were deposited at the NCIMB under accession number NCIMB 42137.

4. A pepper plant of any one of the paragraph 1-3, wherein the novel flavor is defined as the pepper fruits produced by said plant having higher scores for one or more flavor attributes selected from the group consisting of aroma, flowers, non-pungent spices, celery, and chives, and/or a lower score for the flavor attribute grassiness, and optionally a higher odor intensity, as compared to pepper fruits of a similar ripening stage from isogenic pepper plants not carrying said QTL.

5. A pepper plant, of any one of the paragraphs 1-4, wherein the fruits of the pepper plant have a higher amount of artemisia ketone and/or a higher amount of 6-methyl-4-oxo-5-heptenal and/or a higher amount of (E)-2-hexenal and/or a higher amount of (Z)-2-hexen-1-ol and/or a higher amount of 1-penten-3-ol and/or a higher amount of hexanal and/or a higher amount of (Z)-2-penten-1-ol and/or a higher amount of (E)-2-pentenal and/or a lower amount of (Z)-butanoic acid 3-hexenyl ester and/or a lower amount of 2-isobutyl-3-methoxypyrazine compared to fruits of a similar ripening stage from an isogenic pepper plant not comprising said QTL.

6. Seed of a pepper plant of any one of the paragraphs 1-5, comprising the QTL as defined in any of the paragraphs 1-3, which QTL is preferably homozygously present.

7. Seed capable of growing into a pepper plant of any of the paragraphs 1-5, comprising the QTL as defined in any one of the paragraphs 1-3, which QTL is preferably homozygously present.

8. Progeny of a pepper plant of any one of the paragraphs 1-5 or progeny of a pepper plant grown from seed of paragraph 6 or 7, wherein the progeny of the plant comprises the QTL as defined in any of the paragraph 1-3, which QTL is preferably homozygously present.

9. Propagation material derived from a pepper plant of any one of the paragraphs 1-5 or 8 or derived from pepper seed of paragraph 6 or 7, wherein the propagation material comprises the QTL as defined in any of the paragraphs 1-3, which QTL is preferably homozygously present.

10. Propagation material capable of growing into a pepper plant of any one of the paragraphs 1-5, comprising the QTL as defined in any one of the paragraphs 1-3, which QTL is preferably homozygously present.

11. Propagation material of paragraph 9 or 10, wherein the propagation material is selected from the group consisting of callus, microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts or tissue culture thereof.

12. A pepper fruit, or parts thereof, from a pepper plant of any one of the paragraphs 1-5, or grown from seed of paragraph 6 or 7, comprising the QTL as defined in any of the paragraphs 1-3, wherein the QTL is preferably homozygously present.

13. A food product or a processed food product comprising a pepper fruit or a part thereof of paragraph 12.

14. Use of a pepper plant of any one of the paragraphs 1-5 as germplasm in a breeding program for the development of pepper plants comprising a QTL that leads to the novel flavor as defined in paragraph 4 or 5.

15. A nucleic acid or a part thereof, optionally in isolated form, which causes a novel flavor in a pepper fruit, which nucleic acid originates from LG3 of a *Capsicum baccatum* plant or a pepper plant of any one of the paragraphs 1-5, and is linked thereon to at least one of the molecular markers selected from the group of SEQ ID No:1, SEQ ID No:3, SEQ ID No:5, SEQ ID No:7, SEQ ID No:9 and SEQ ID No:11.

16. Use of a molecular marker selected from the group consisting of SEQ ID No:1, SEQ ID No:3, SEQ ID No:5, SEQ ID No:7, SEQ ID No:9 and SEQ ID No:11 to identify or develop pepper plants producing fruits with a novel flavor, in particular as in paragraph 4 and/or paragraph 5, and/or identify the QTL located on LG3 in a pepper plant as in any of the paragraphs 1-3, and/or to develop other markers linked to the QTL on LG3 as in any of the paragraphs 1-3.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

| SEQUENCE LISTING |
| --- |

```
<110> Rijk Zwaan Zaadteelt en Zaadhandel B.V.

<120> PEPPER WITH NOVEL FLAVOR

<130> L/2QJ24/KK/232

<150> EP13174795.8
<151> 2013-07-02

<160> 12

<170> BiSSAP 1.2

<210> 1
<211> 96
<212> DNA
<213> Capsicum baccatum

<220>
<221> source
<222> 1..96
```

SEQUENCE LISTING

<223> /organism="Capsicum baccatum"/mol_type="unassigned DNA"

<400> 1
gagtggcagt gattttttct gatagcaaca acgcacctat tgagagattt gttttcaaga    60
taaatgtgaa ccagtcctat ggttcgaagt tggagg                              96

<210> 2
<211> 96
<212> DNA
<213> Capsicum annuum

<220>
<221> source
<222> 1..96
<223> /organism="Capsicum annuum"/mol_type="unassigned DNA"

<400> 2
gagtggcagt gattttttct gatagcaaca acgcacctat tgagagattt attttcaaga    60
taaatgtgaa ccagtcctat ggttcgaagt tggagg                              96

<210> 3
<211> 101
<212> DNA
<213> Capsicum baccatum

<220>
<221> source
<222> 1..101
<223> /organism="Capsicum baccatum"/mol_type="unassigned DNA"

<400> 3
gggatgaaag aaaagctaga ttctagaaaa ttggtgatgg gaaacatgtc aatgcattct    60
aaagtagtca aagagaaagt caagaagcaa gaggagcaac t                       101

<210> 4
<211> 101
<212> DNA
<213> Capsicum annuum

<220>
<221> source
<222> 1..101
<223> /organism="Capsicum annuum"/mol_type="unassigned DNA"

<400> 4
gggatgaaag aaaagctaga ttctagaaaa ttggtgatgg gaaacatgtc agtgcattct    60
aaagtagtca aagagaaagt caagaagcaa gaggagcaac t                       101

<210> 5
<211> 99
<212> DNA
<213> Capsicum baccatum

<220>
<221> source
<222> 1..99
<223> /organism="Capsicum baccatum"/mol_type="unassigned DNA"

<400> 5
cacttctcaa atgcttaaag gccattagag accacgcttt tgttaagtcg ccttatcctg    60
tcataatcac gttggaagac cacttgacac cagatcttc                           99

<210> 6
<211> 99
<212> DNA
<213> Capsicum annuum

<220>
<221> source
<222> 1..99
<223> /organism="Capsicum annuum"/mol_type="unassigned DNA"

SEQUENCE LISTING

```
<400> 6
cacttctcaa atgcttaaag gccattagag accacgcttt tgttaagtcg tcttatcctg    60
tcataatcac gttggaagac cacttgacac cagatcttc                           99

<210> 7
<211> 78
<212> DNA
<213> Capsicum baccatum

<220>
<221> source
<222> 1..78
<223> /organism="Capsicum baccatum"/mol_type="unassigned DNA"

<400> 7
cattataaca catccagtat acaaaataaa cactcccaga tttagagtaa ccaaatttcc    60
aaaacaatac cgaaagcc                                                  78

<210> 8
<211> 78
<212> DNA
<213> Capsicum annuum

<220>
<221> source
<222> 1..78
<223> /organism="Capsicum annuum"/mol_type="unassigned DNA"

<400> 8
cattataaca catccagtat acaaaataag cactcccaga tttagagtaa ccaaatttcc    60
aaaacaatac cgaaagcc                                                  78

<210> 9
<211> 160
<212> DNA
<213> Capsicum baccatum

<220>
<221> source
<222> 1..160
<223> /organism="Capsicum baccatum"/mol_type="unassigned DNA"

<400> 9
cgcctaagcg cacacacaag tgtacgtggt ctaccaagta ttwaaacctt tcaacctcac    60
ttgaggcctt atacttcact ttatatatcc acctgcaacc aatagccttc tttcctttag  120
gtagagcaac aatctcccaa gtatgattgg aattcaaggc                         160

<210> 10
<211> 160
<212> DNA
<213> Capsicum annuum

<220>
<221> source
<222> 1..160
<223> /organism="Capsicum annuum"/mol_type="unassigned DNA"

<400> 10
cgcctaagcg cacacacaag tgtacgtggt ctaccaagta ttwaaacctt tcaacctcac    60
ttgaggcctt atacttcact ttatatatcc acctgcaacc aatagcttc tttcctttag   120 gtagagcaac aatctcccaa gtatgattgg aattcaaggc                         160

<210> 11
<211> 110
<212> DNA
<213> Capsicum baccatum

<220>
<221> source
<222> 1..110
```

-continued

SEQUENCE LISTING

<223> /organism="Capsicum baccatum"/mol_type="unassigned DNA"

<400> 11
ggagaagctt ggtcctcaac tcgccattat tgctccgatc aagtactgag gtcgaaatat    60
agtttgtttc aagtaaaatt ttgatggagg ttgatgtttt ggcattagtg              110

<210> 12
<211> 110
<212> DNA
<213> Capsicum annuum

<220>
<221> source
<222> 1..110
<223> /organism="Capsicum annuum"/mol_type="unassigned DNA"

<400> 12
ggagaagctt ggtcctcaac tcgccattat tgctccgatc aagtactgag gtcgaagtat    60
agtttgtttc aagtaaaatt ttgatggagg ttgatgtttt ggcattagtg              110

SEQUENCE LISTING

<160> NUMBER OF SEQ ID NOS: 12

<210> SEQ ID NO 1
<211> LENGTH: 96
<212> TYPE: DNA
<213> ORGANISM: Capsicum baccatum
<220> FEATURE:
<221> NAME/KEY: source
<222> LOCATION: 1..96
<223> OTHER INFORMATION: /organism="Capsicum baccatum"
      /mol_type="unassigned DNA"

<400> SEQUENCE: 1
gagtggcagt gattttttct gatagcaaca acgcacctat tgagagattt gttttcaaga    60
taaatgtgaa ccagtcctat ggttcgaagt tggagg                              96

<210> SEQ ID NO 2
<211> LENGTH: 96
<212> TYPE: DNA
<213> ORGANISM: Capsicum annuum
<220> FEATURE:
<221> NAME/KEY: source
<222> LOCATION: 1..96
<223> OTHER INFORMATION: /organism="Capsicum annuum"
      /mol_type="unassigned DNA"

<400> SEQUENCE: 2
gagtggcagt gattttttct gatagcaaca acgcacctat tgagagattt attttcaaga    60
taaatgtgaa ccagtcctat ggttcgaagt tggagg                              96

<210> SEQ ID NO 3
<211> LENGTH: 101
<212> TYPE: DNA
<213> ORGANISM: Capsicum baccatum
<220> FEATURE:
<221> NAME/KEY: source
<222> LOCATION: 1..101
<223> OTHER INFORMATION: /organism="Capsicum baccatum"
      /mol_type="unassigned DNA"

<400> SEQUENCE: 3
gggatgaaag aaaagctaga ttctagaaaa ttggtgatgg gaaacatgtc aatgcattct    60
aaagtagtca aagagaaagt caagaagcaa gaggagcaac t                           101

<210> SEQ ID NO 4
<211> LENGTH: 101
<212> TYPE: DNA
<213> ORGANISM: Capsicum annuum
<220> FEATURE:
<221> NAME/KEY: source
<222> LOCATION: 1..101
<223> OTHER INFORMATION: /organism="Capsicum annuum"
      /mol_type="unassigned DNA"

<400> SEQUENCE: 4
gggatgaaag aaaagctaga ttctagaaaa ttggtgatgg gaaacatgtc agtgcattct        60
aaagtagtca agagaaagt caagaagcaa gaggagcaac t                            101

<210> SEQ ID NO 5
<211> LENGTH: 99
<212> TYPE: DNA
<213> ORGANISM: Capsicum baccatum
<220> FEATURE:
<221> NAME/KEY: source
<222> LOCATION: 1..99
<223> OTHER INFORMATION: /organism="Capsicum baccatum"
      /mol_type="unassigned DNA"

<400> SEQUENCE: 5
cacttctcaa atgcttaaag gccattagag accacgcttt tgttaagtcg ccttatcctg        60
tcataatcac gttggaagac cacttgacac cagatcttc                              99

<210> SEQ ID NO 6
<211> LENGTH: 99
<212> TYPE: DNA
<213> ORGANISM: Capsicum annuum
<220> FEATURE:
<221> NAME/KEY: source
<222> LOCATION: 1..99
<223> OTHER INFORMATION: /organism="Capsicum annuum"
      /mol_type="unassigned DNA"

<400> SEQUENCE: 6
cacttctcaa atgcttaaag gccattagag accacgcttt tgttaagtcg tcttatcctg        60
tcataatcac gttggaagac cacttgacac cagatcttc                              99

<210> SEQ ID NO 7
<211> LENGTH: 78
<212> TYPE: DNA
<213> ORGANISM: Capsicum baccatum
<220> FEATURE:
<221> NAME/KEY: source
<222> LOCATION: 1..78
<223> OTHER INFORMATION: /organism="Capsicum baccatum"
      /mol_type="unassigned DNA"

<400> SEQUENCE: 7
cattataaca catccagtat acaaaataaa cactcccaga tttagagtaa ccaaatttcc        60
aaaacaatac cgaaagcc                                                     78

<210> SEQ ID NO 8
<211> LENGTH: 78
<212> TYPE: DNA
<213> ORGANISM: Capsicum annuum
<220> FEATURE:
<221> NAME/KEY: source
<222> LOCATION: 1..78

```
<223> OTHER INFORMATION: /organism="Capsicum annuum"
      /mol_type="unassigned DNA"

<400> SEQUENCE: 8
cattataaca catccagtat acaaaataag cactcccaga tttagagtaa ccaaatttcc      60
aaaacaatac cgaaagcc                                                   78

<210> SEQ ID NO 9
<211> LENGTH: 160
<212> TYPE: DNA
<213> ORGANISM: Capsicum baccatum
<220> FEATURE:
<221> NAME/KEY: source
<222> LOCATION: 1..160
<223> OTHER INFORMATION: /organism="Capsicum baccatum"
      /mol_type="unassigned DNA"

<400> SEQUENCE: 9
cgcctaagcg cacacacaag tgtacgtggt ctaccaagta ttwaaacctt tcaacctcac      60
ttgaggcctt atacttcact ttatatatcc acctgcaacc aatagccttc tttcctttag    120
gtagagcaac aatctcccaa gtatgattgg aattcaaggc                          160

<210> SEQ ID NO 10
<211> LENGTH: 160
<212> TYPE: DNA
<213> ORGANISM: Capsicum annuum
<220> FEATURE:
<221> NAME/KEY: source
<222> LOCATION: 1..160
<223> OTHER INFORMATION: /organism="Capsicum annuum"
      /mol_type="unassigned DNA"

<400> SEQUENCE: 10
cgcctaagcg cacacacaag tgtacgtggt ctaccaagta ttwaaacctt tcaacctcac      60
ttgaggcctt atacttcact ttatatatcc acctgcaacc aatagctttc tttcctttag    120
gtagagcaac aatctcccaa gtatgattgg aattcaaggc                          160

<210> SEQ ID NO 11
<211> LENGTH: 110
<212> TYPE: DNA
<213> ORGANISM: Capsicum baccatum
<220> FEATURE:
<221> NAME/KEY: source
<222> LOCATION: 1..110
<223> OTHER INFORMATION: /organism="Capsicum baccatum"
      /mol_type="unassigned DNA"

<400> SEQUENCE: 11
ggagaagctt ggtcctcaac tcgccattat tgctccgatc aagtactgag gtcgaaatat      60
agtttgtttc aagtaaaatt ttgatggagg ttgatgtttt ggcattagtg               110

<210> SEQ ID NO 12
<211> LENGTH: 110
<212> TYPE: DNA
<213> ORGANISM: Capsicum annuum
<220> FEATURE:
<221> NAME/KEY: source
<222> LOCATION: 1..110
```

```
<223> OTHER INFORMATION: /organism="Capsicum annuum"
       /mol_type="unassigned DNA"

<400> SEQUENCE: 12
ggagaagctt ggtcctcaac tcgccattat tgctccgatc aagtactgag gtcgaagtat        60
agtttgtttc aagtaaaatt ttgatggagg ttgatgtttt ggcattagtg                  110
```

What is claimed is:

1. A *Capsicum annuum* plant that produces fruits with an altered flavor, wherein the plant is a sweet pepper plant and comprises a QTL from *Capsicum baccatum* var. *pendulum* which when present leads to the altered flavor, wherein the QTL is located on LG3 and wherein said QTL is present in the genome of plants grown from seeds deposited under accession number NCIMB 42137;

wherein said altered flavor is compared to pepper fruits of a similar ripening stage from isogenic *Capsicum annuum* pepper plants not carrying said QTL;

and wherein said *Capsicum annuum* plant comprising said QTL from *Capsicum baccatum* also comprises SEQ ID No:1, SEQ ID No:3, SEQ ID No:5, SEQ ID No:7, SEQ ID No:9 and SEQ ID No. 11.

2. The plant of claim 1, wherein the QTL is homozygously present.

3. The plant of claim 1, wherein the altered flavor is defined as the pepper fruits produced by said plant having higher scores for one or more flavor attributes comprising an aroma, flower, non-pungent spice, celery and/or a chive; and/or a lower score for the flavor attribute grassiness; as compared to pepper fruits of a similar ripening stage from isogenic *Capsicum annuum* pepper plants not carrying said QTL.

4. The plant of claim 3, comprising a higher odor intensity, as compared to pepper fruits of a similar ripening stage from isogenic *Capsicum annuum* pepper plants not carrying said QTL.

5. The plant of claim 1, wherein the fruit of the pepper plant has a higher amount of artemisia ketone and/or a higher amount of 6-methyl-4-oxo-5-heptenal and/or a higher amount of (E)-2-hexenal and/or a higher amount of (Z)-2-hexen-1-ol and/or a higher amount of 1-penten-3-ol and/or a higher amount of hexanal and/or a higher amount of (Z)-2-penten-1-ol and/or a higher amount of (E)-2-pentenal and/or a lower amount of (Z)-butanoic acid 3-hexenyl ester and/or a lower amount of 2-isobutyl-3-methoxypyrazine compared to a fruit of a similar ripening stage from an isogenic pepper plant not comprising said QTL.

6. A seed deposited at the NCIMB under accession number 42137 comprising the QTL of claim 1.

7. The seed of claim 6, wherein the QTL is homozygously present.

8. A seed capable of growing into the plant of claim 1 comprising the QTL.

9. The seed of claim 8, wherein the QTL is homozygously present.

10. A *Capsicum annuum* progeny of the plant of claim 1, wherein the progeny comprises the QTL of claim 1.

11. The progeny of claim 10, wherein the QTL is homozygously present.

12. A *Capsicum annuum* progeny of a plant grown from the seed of claim 6, wherein the progeny comprises the QTL of claim 1.

13. The progeny of claim 12, wherein the QTL is homozygously present.

14. A *Capsicum annuum* progeny of a plant grown from the seed of claim 8, wherein the progeny comprises the QTL of claim 1.

15. The progeny of claim 14, wherein the QTL is homozygously present.

16. A *Capsicum annuum* propagation material derived from the plant of claim 1, wherein the propagation material comprises the QTL of claim 1.

17. The propagation material of claim 16, wherein the QTL is homozygously present.

18. A *Capsicum annuum* propagation material derived from the seed of claim 6, wherein the propagation material comprises the QTL of claim 1.

19. The propagation material of claim 18, wherein the QTL is homozygously present.

20. A *Capsicum annuum* propagation material derived from the seed of claim 8, wherein the propagation material comprises the QTL of claim 1.

21. The propagation material of claim 20, wherein the QTL is homozygously present.

22. A *Capsicum annuum* propagation material capable of growing into the plant of claim 1, wherein the propagation material comprises the QTL.

23. The propagation material of claim 22, wherein the QTL is homozygously present.

24. The propagation material of claim 16, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

25. The propagation material of claim 18, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

26. The propagation material of claim 20, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

27. The propagation material of claim 22, wherein the propagation material comprises a callus, microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed or stem; or a part or tissue culture thereof.

28. A pepper fruit, or a part thereof, from the plant of claim 1, wherein the pepper fruit or part thereof comprises the QTL.

29. The fruit of claim 28, wherein the QTL is homozygously present.

30. A pepper fruit, or a part thereof, from a plant grown from the seed of claim 6; comprising the QTL.

31. The fruit of claim 30, wherein the QTL is homozygously present.

32. A pepper fruit, or a part thereof, from a plant grown from the seed of claim 8; comprising the QTL.

33. The fruit of claim 32, wherein the QTL is homozygously present.

* * * * *